(12) United States Patent
Hour et al.

(10) Patent No.: US 9,045,437 B2
(45) Date of Patent: *Jun. 2, 2015

(54) 2-ARYL-4-QUINAZOLINONES AND THEIR PHARMACEUTICAL COMPOSITIONS

(71) Applicant: China Medical University, Taichung (TW)

(72) Inventors: Mann-Jen Hour, Taichung (TW); Po-Wu Gean, Tainan (TW); Sheng-Chu Kuo, Taichung (TW); Hong-Zin Lee, Taichung (TW); Jai-Sing Yang, Hualien (TW); Li-Chen Chou, Taichung (TW); Tai-Lin Chen, Taipei (TW); Yang-Chang Wu, Taichung (TW)

(73) Assignee: China Medical University, Taichung (TW)

( * ) Notice: Subject to any disclaimer, the term of this patent is extended or adjusted under 35 U.S.C. 154(b) by 9 days.

This patent is subject to a terminal disclaimer.

(21) Appl. No.: 13/953,882

(22) Filed: Jul. 30, 2013

(65) Prior Publication Data

US 2013/0310376 A1    Nov. 21, 2013

Related U.S. Application Data

(62) Division of application No. 13/277,520, filed on Oct. 20, 2011, now Pat. No. 8,710,064.

(51) Int. Cl.
*C07D 239/91* (2006.01)
*C07D 403/04* (2006.01)
*C07D 409/04* (2006.01)

(52) U.S. Cl.
CPC ............ *C07D 239/91* (2013.01); *C07D 403/04* (2013.01); *C07D 409/04* (2013.01)

(58) Field of Classification Search
None
See application file for complete search history.

(56) References Cited

U.S. PATENT DOCUMENTS

8,710,064 B2 * 4/2014 Hour et al. .................. 514/266.2
2008/0188467 A1 * 8/2008 Wong et al. ................ 514/224.2

* cited by examiner

*Primary Examiner* — James D Anderson
(74) *Attorney, Agent, or Firm* — Fishman & Associates, LLC.

(57) ABSTRACT

Provided is a compound of the formula I or a pharmaceutically acceptable salt, solvate or stereoisomer thereof:

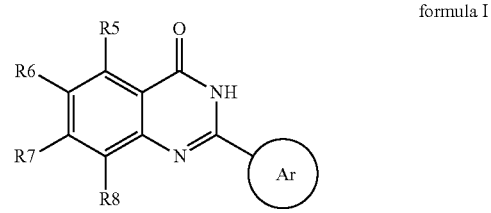

formula I wherein Ar represents

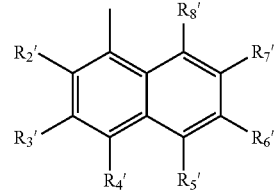

$R_5$, $R_7$, $R_8$, $R_2'$, $R_3'$, $R_4'$, $R_5'$, $R_6'$, $R_7'$, $R_8'$ independently represent H, OH, F, Cl, Br methoxyl group, $NH_2$ group or $NMe_2$ group; X represents NH, O or S; $R_6$ is selected from the group consisting of: piperidinyl group, morpholino group, methoxyl group, and dimethylamine group. The present invention also provides a composition comprising the compound of formula I. The compound and the composition in accordance with the present invention are effective on treating or alleviating a disease or disorder, such as malignant glioma.

7 Claims, 2 Drawing Sheets

2-ARYL-4-QUINAZOLINONES AND THEIR PHARMACEUTICAL COMPOSITIONS

BACKGROUND OF THE INVENTION

1. Field of the Invention

The present invention relates to 2-aryl-4-quinazolinones and pharmaceutical compositions comprising the same for treating cancer, particularly for malignant gliomas.

2. Description of the Prior Arts

Primary brain and spinal cord tumors are among the top 10 causes of deaths due to cancer with over 16,000 people dying from them each year in the United States. Malignant gliomas account for approximately 70% of the 22,500 new cases of malignant primary brain tumor that are diagnosed in adults in the United States each year. Although the prevalence of malignant glioma is relative lower than that of the other cancers such as lung, breast, prostate, colorectal, and liver cancers, malignant glioma has high mortality. In Taiwan, the frequencies of death of malignant brain tumor hit 1.06% in men and 1.45% in women, ranked the $15^{th}$ and $13^{th}$ respectively. Glioblastoma multiforme (GBM) defined by WHO as grade IV is the most common and most aggressive type of glioma in humans. Despite optimal treatment, the median survival is only 12 to 15 months for patients with glioblastomas. Despite recent advances in surgery, radiotherapy, and chemotherapy, the prognosis of patients diagnosed with malignant gliomas remains very poor. The current technique lacks a compound with profound efficacy on gliomas. Therefore, the development of the new anti-malignant glioma drugs is urgently needed.

SUMMARY OF THE INVENTION

Given the need of solution for gliomas, the objective of the present invention is to provide a novel compound and composition that have profound efficacy on gliomas.

Accordingly, the present invention provides a compound of the formula I:

formula I wherein $R_5$, $R_6$, $R_7$ and $R_8$ independently represent H, OH, F, Cl, Br, $C_1$ to $C_6$ alkyl group, $C_1$ to $C_6$ alkoxy group, $C_2$ to $C_6$ alkenyl group, $C_2$ to $C_6$ alkenoxy group, $C_2$ to $C_6$ alkynyl group, $C_2$ to $C_6$ alkynoxy group, amine group, mono- or di-substituted amino group, cyclic $C_1$ to $C_5$ alkylamino group, imidazolyl group, morpholino group, piperazinyl group, optionally substituted with one or more hydroxy or halo; Ar represents $R_1'$, $R_2'$, $R_3'$, $R_4'$, $R_5'$, $R_6'$, $R_7'$, $R_8'$ independently represent H, OH, F, Cl, Br, $C_1$ to $C_6$ alkyl group, $C_1$ to $C_6$ alkoxy group, $C_2$ to $C_6$ alkenyl group, $C_2$ to $C_6$ alkenoxy group, $C_2$ to $C_6$ alkynyl group, $C_2$ to $C_6$ alkynoxy group, amine group, mono- or di-substituted amino group, cyclic $C_1$ to $C_5$ alkylamino group, imidazolyl group, morpholino group, piperazinyl group, optionally substituted with one or more hydroxy or halo; X represents NH, O or S; or a pharmaceutically acceptable salt, solvate or stereoisomer thereof.

In another aspect, the present invention provides a composition comprising a compound provided herein and a carrier.

In another aspect, the present invention provides a method for treating diseases or disorders comprising: administering the compound of the formula I or composition comprising the same to a subject in need thereof.

Other objectives, advantages and novel features of the invention will become more apparent from the following detailed description when taken in conjunction with the accompanying drawings.

DETAILED DESCRIPTION OF THE PREFERRED EMBODIMENTS

In one embodiment, provided is 2-aryl-4-quinazolinone or a pharmaceutically acceptable salt, solvate or stereoisomer thereof.

In another embodiment, provided is a composition, which comprises the 2-aryl-4-quinazolinone or a pharmaceutically acceptable salt, solvate or stereoisomer thereof; and a carrier.

In another embodiment, provided is a method for treating or alleviating diseases or disorders, comprising administering the 2-aryl-4-quinazolinone or its pharmaceutically acceptable salt, solvate or stereoisomer to a subject in need thereof.

In a preferred embodiment, the 2-aryl-4-quinazolinone is the compound of the formula I:

formula I wherein $R_5$, $R_6$, $R_7$ and $R_8$ independently represent H, OH, F, Cl, Br, $C_1$ to $C_6$ alkyl group, $C_1$ to $C_6$ alkoxy group, $C_2$ to $C_6$ alkenyl group, $C_2$ to $C_6$ alkenoxy group, $C_2$ to $C_6$ alkynyl group, $C_2$ to $C_6$ alkynoxy group, amine group, mono- or di-substituted amino group, cyclic $C_1$ to $C_5$ alkylamino group, imidazolyl group, morpholino group, piperazinyl group, optionally substituted with one or more hydroxy or halo; Ar represents $R_1'$, $R_2'$, $R_3'$, $R_4'$, $R_5'$, $R_6'$, $R_7'$, $R_8'$ independently represent H, OH, F, Cl, Br, $C_1$ to $C_6$ alkyl group, $C_1$ to $C_6$ alkoxy group, $C_2$ to $C_6$ alkenyl group, $C_2$ to $C_6$ alkenoxy group, $C_2$ to $C_6$ alkynyl group, $C_2$ to $C_6$ alkynoxy group, amine group, mono- or di-substituted amino group, cyclic $C_1$ to $C_5$ alkylamino group, imidazolyl group, morpholino group, piperazinyl group, optionally substituted with one or more hydroxy or halo; and X represents NH, O or S.

The term "$C_1$ to $C_6$ alkyl" as used herein refers to a branched or unbranched alkyl group having 1 to 6 carbon atoms. For example, such group is methyl, ethyl, isopropyl, tertiary-butyl, pentyl or hexyl group. Similarly the term "$C_1$ to $C_2$ alkyl" as used herein refers to an alkyl group having 1 to 2 carbon atoms.

The term "$C_2$ to $C_6$ alkenyl" as used herein refers to a branched or unbranched alkenyl group having 2 to 6 carbon atoms and at least one double bond. For example, such group is ethenyl or isopropenyl.

The term "$C_2$ to $C_6$ alkynyl" as used herein refers to a branched or unbranched alkynyl group having 2-6 carbon atoms and at least one triple bond. For example, such group is ethynyl or 3-methyl-1-butylyl.

The term "mono-substituted amine group" as used herein refers to primary amine group with a branched or unbranched alkyl substitute. Likewise, the term "di-substituted amine group" as used herein refers to secondary amine group with a branched or unbranched alkyl substitute. In a preferred embodiment, di-substituted amino group is dimethylamine group.

Preferably, said cyclic $C_1$ to $C_5$ alkylamino group includes, but not limited to, pyridinyl group, pyrrolidinyl group, piperidinyl group and morpholino group.

In one embodiment, Ar is naphthalenyl group. In another embodiment, Ar is indolyl group. In still another embodiment, Ar is benzothiophenyl group.

In one embodiment, $R_6$ is hydrogen group. In another embodiment, $R_6$ is methoxyl group. In another embodiment, $R_6$ is dimethylamino group. In another embodiment, $R_6$ is pyrrolidinyl group. In still another embodiment, $R_6$ is piperidinyl group. In yet another embodiment, $R_6$ is morpholino group.

Specific examples of the compound in accordance with the present invention are, but not limited to:

The term "pharmaceutically acceptable salt" as used herein refers to acid addition salts prepared from non-toxic acid and base salts prepared from non-toxic base. Suitable acids include, but not limited to, acetic, alginic, anthranilic, benzenesulfonic, benzoic, camphorsulfonic, citric, ethenesulfonic, formic, fumaric, furoic, gluconic, glutamic, glucorenic, galacturonic, glycidic, hydrobromic, hydrochloric, isethionic, lactic, maleic, malic, mandelic, methanesulfonic, mucic, nitric, pamoic, pantothenic, phenylacetic, propionic, phosphoric, salicylic, stearic, succinic, sulfanilic, sulfuric, tartaric acid, p-toluenesulfonic and the like. In one embodiment, suitable acids are hydrochloric, hydrobromic, phosphoric, and sulfuric acids.

Suitable bases include, but not limited to, alkali metal cations such as potassium and sodium hydroxide; alkaline earth metal cations such as calcium and magnesium; ammonium or water-soluble amine and the lower alkanolammonium. Particularly, suitable bases include aluminium, arginine, benzathine, calcium, choline, diethylamine, diolamine, glycine, lysine, tromethamine and hydroxide of magnesium, meglumine, olamine, potassium, sodium or zinc.

The term "solvate" as used herein refers to a complex of variable stoichiometry formed by a solvent and a solute, which is a compound of formula I in the present invention. Such solvent has little interference with the biological activity of the solute. For example, suitable solvents include water, methanol, ethanol and acetic acid. Preferably, the solvent is a pharmaceutically acceptable solvent, such as water, ethanol and acetic acid.

The compound of the formula I in accordance with the present invention can be in all stereoisomeric forms. Said stereoisomeric forms are such as enantiomers, diastereoisomers, and cis- and trans-isomers. For example, in the case where $R_6$ is alkenyl group, both (Z) and (E) stereoisomeric forms of the compound are applicable.

For geometrical isomers of the compound in accordance with the present invention, methods for preparing geometrical isomers are also well known in the art. For chiral isomers of the compound in accordance with the present invention, methods for preparing pure stereoisomers are well known in the art, such as synthesis with a chiral starting compound, chiral induction, enantioselective enzymatic conversions and chromatography of stereoisomers on chiral media.

The compounds of the formula I in accordance with the present invention can be in all isotopically labeled forms. For example, such compounds are labeled with $_2H$, $_3H$, $_{11}C$, $_{13}C$, $_{14}C$, $_{131}I$, $_{125}I$, $_{123}I$ and $_{18}F$. The labeled compounds are for use in tracing a marker molecule in various diagnoses in vitro or in vivo.

In a preferred embodiment, the composition comprises the compound of the formula I or a pharmaceutically acceptable salt, solvate or stereoisomer thereof; and a carrier.

The carrier hereby refers to any substance that is pharmaceutically acceptable and, preferably, for assisting compound's in vivo absorption and releasing in a sustained manner or other manners to modulate the metabolic kinetics of compound in a subject.

The term "pharmaceutically acceptable carrier" refers to various organic or inorganic carrier substances conventionally used as preparation materials. For example, excipient, disintegrant, binder, glidant, lubricant and the like for solid dosage forms, and for liquid preparations, solvent, solubilizing agent, suspending agent, isotonicity agent, buffer, soothing agent and the like are used. If required, additives such as preservative, antioxidant, colorant, sweetening agent and the like are used.

In a preferred embodiment of the method for treating or alleviating diseases or disorders in accordance with the present invention, the diseases or disorders include, but not limited to, skin, lung, lymph node, breast, cervix, uterus, gastrointestinal tract, ovary, prostate, colorectal, mouth, brain, head and neck, throat, testes, kidney, pancreas, bone, spleen, liver, bladder, larynx and nasal passage cancers or tumors.

Particularly, the cancers or tumors include, but not limited to, malignant gliomas and other sarcoma, carcinoma, adenoma and so on.

In a preferred embodiment, provided is a method for treating or alleviating malignant glioma, which has the following steps: administering the compound or a pharmaceutically acceptable salt, solvate or stereoisomer thereof in accordance with the present invention to a subject suffering from malignant glioma.

In a preferred embodiment, the compound or a pharmaceutically acceptable salt, solvate or stereoisomer thereof in accordance with the present invention can be combined with other pharmacologically active compound in methods and compositions in accordance with the present invention.

In general, the compound of formula I in accordance with the present invention encompassing a series of 2-aryl-4-quinazolinones, which were newly synthesized and exhibited significant anti-proliferative effects to many kinds of human cancer cells. More specifically, 2-aryl-4-quinazolinones display favorable in vivo and in vitro activity against malignant gliomas. 6-(Pyrrolidin-1-yl)-2-(naphthalen-1-yl)quinazolin-4-one, one of the 2-aryl-4-quinazolinones, displays excellent activity against malignant gliomas and is an anti-malignant glioma candidate.

In the following Examples, a series of novel 2-aryl-4-quinazolinones have been synthesized and displayed potent anti-cancer activity in vitro cancer cells and in vivo animal model. These cancer cells include human malignant melanoma (M21), human lung squamous carcinoma (CH27), human hepatocellular carcinoma (Hep3B), lung non-small carcinoma (H460) cells, human oral squamous cell carcinoma (HSC-3), human colon adenocarcinoma (HT29-5FUR), human glioma cells (U87, U251, T98G, U373) and rat glioma cells (C6, RT2). Among these novel synthetic 2-aryl-4-quinazolinones, 6-(pyrrolidin-1-yl)-2-(naphthalen-1-yl)quinazolin-4-one (compound 23, that is, MJ-66) is the most potent compound that showed significant cytotoxicity against a panel of human tumor cell lines with $IC_{50}$ values in the low micromolar to nanomolar concentration ranges. For example, compound 23 was shown being capable of inhibiting the growth of human malignant melanoma and glioma cells in vitro with $IC_{50}$ about 33 nM and 60 nM respectively. In addition, compound 23 was demonstrated being capable of inhibiting tumor growth in glioma xenograft animal model. Therefore, the novel synthetic 2-aryl-4-quinazolinones and their pharmaceutical compositions in accordance with the present invention are potent for treating cancers. More specifically, 2-aryl-4-quinazolinones display favorable in vivo and in vitro activity against malignant gliomas and are suitable for treating human malignant gliomas.

EXAMPLES

General Materials and Method

1. Materials and Reagents

All of the solvents and reagents were obtained commercially and used without further purification. Reaction progress was monitored by thin-layer chromatography, using Merck TLC plates with fluorescent indicator. Column chromatography was performed on silica gel. Melting points were determined with a Yanaco MP-500D melting point apparatus and are uncorrected. NMR spectra were obtained on a Bruker Avance DPX-200 FT-NMR spectrometer in DMSO-$d_6$. The following abbreviations are used: mp, melting point, s, singlet; d, doublet; dd, double doublet; t, triplet; q, quartet; in, multiplet; and br, broad. MS spectra were measured with a Finnigan/Thermo Quest MAT 95XL instrument. Elemental analyses (C, H, and N) were performed on a Perkin-Elmer 2400 Series II CHNS/O analyzer or Elementar vario EL III Heraeus CHNOS Rapid F002 and the results were within ±0.4% of the calculated values.

MTS (3-(4,5-dimethylthiazol-2-yl)-5-(3-carboxymethoxyphenyl)-2-(4-sulfophenyl)-2H-tetrazolium), MTT (3-[4,5-dimethylthiazol-2-yl]-2,5-diphenyltetrazolium bromide), N-acetylcysteine (NAC), cyclosporine A and dimethyl sulfoxide (DMSO) were purchased from SigmaeAldrich Corp. (St. Louis, Mo., USA). Fetal bovine serum (FBS), L-glutamine, penicillin-streptomycin, RPMI 1640 medium, Dulbecco's modified eagle medium (DMEM), Minimum Essential Medium (MEM) (Invitrogen), F12 mediem, trypsin-EDTA, Neuralbasal A medium (Gibco).

2. Cell Culture

M21 cell line (human malignant melanoma) was provided by Dr. Feng-Yao Tang (China Medical University, Taiwan). Cells were grown in monolayer culture in RPMI-1640 medium, Eagle's minimum essential medium or Dulbecco's modified Eagles medium (Invitrogen Corporation, Grand Island, N.Y., USA) containing 10% fetal bovine serum (FBS; HyClone, Logan, Utah, USA), 100 U/ml penicillin and 100 μg/ml streptomycin (Gibco BRL, Rockville, Md., USA).

CH27 cells (Human lung squamous carcinoma) were grown in monolayer culture in Dulbecco's modified Eagle's medium (DMEM; Life Technologies, Rockville, Md., USA) containing 5% FBS (HyClone, Logan, Utah, USA), 100 U/ml penicillin, 100 μg/ml streptomycin (Gibco BRL, Rockville, Md., USA) and 2 mM glutamine (Merck, Darmstadt, Germany).

Hep3B (human hepatocellular carcinoma) and H460 (lung non-small carcinoma) cells were grown in monolayer culture in Dulbecco's modified Eagle's medium (DMEM) (Life Technologies, Rockville, Md., USA) containing 5% fetal bovine serum (HyClone, Logan, Utah, USA), 100 U/ml penicillin and 100 μg/ml streptomycin (Gibco BRL, Rockville, Md., USA) and 2 mM glutamine (Merck, Darmstadt, Germany).

The HSC-3 (human oral squamous cell carcinoma) were cultured in 1:1 Dulbecco's Modified Eagle's Medium (DMEM) and Ham's Nutrient Mixture F-12, containing 10% FBS (HyClone, Logan, Utah, USA), 100 U/ml penicillin, 100 µg/ml streptomycin (Gibco BRL, Rockville, Md., USA) and 2 mM glutamine (Merck, Darmstadt, Germany).

HT29-5FUR cell line (human colon adenocarcinoma) provided by Dr. Jai-Sing Yang (China Medical University, Taiwan) was cultured in RPMI-1640 medium (Invitrogen, Carlsbad, Calif., USA) supplemented with 10% fetal bovine serum, 2 mM L-glutamine, 100 U/ml penicillin, and 100 µg/ml streptomycin.

The human glioma cell lines U87, U251, T98G, U373, and rat glioma cell line RT2 provided by Dr. Michael Hsiao (Genomics Research Center, Academia Sinica, Taiwan) were cultured in Dulbecco's Modified Eagle medium (DMEM) (Caisson) supplemented with 10% fetal bovine serum (FBS) (Sigma-Aldrich), 2 mM L-glutamine (Caisson), 100 U/ml penicillin, and 100 µg/ml streptomycin (Caisson). The rat glioma C6 cell line provided by Dr. Shun-Fen Tzeng (National Cheng Kung University, Taiwan) was cultured in DMEM/F12 (Caisson) supplemented with 10% fetal bovine serum, 2 mM L-glutamine, 100 U/ml penicillin, and 100 µg/ml streptomycin. The human normal glia cell line SVGP12, kindly provided by Dr. Michael Hsiao, was cultured in Minimum Essential Medium (MEM) (Invitrogen) supplemented with 10% fetal bovine serum, 2 mM L-glutamine, 100 U/ml penicillin, and 100 µg/ml. Primary glia cells were prepared by surgery. Cerebral cortices without meninges were dissected from postnatal ($P_0$-$P_2$) Sprague-Dawley (SD, NCKU Laboratory Animal Center) rats and dissociated in 0.05% trypsin-EDTA (Biowest) at 37° C. for 10 min. Culture medium was added and pipetted for several times, and supernatant was removed after a centrifugation at 1,000 rpm for 5 minutes. Glia cells were filtered through 70 µm cell strainer (BD Falcon) and then cultured in Neuralbasal A medium (Gibco) supplemented with 5% fetal bovine serum (Sigma-Aldrich), 2 mM L-glutamine, 100 U/ml penicillin, 100 µg/ml streptomycin and 17.5 mM D-glucose on 50 µg/ml poly-D-lysine (Sigma-Aldrich) pre-coated dish.

All cells were maintained in a humidified incubator at 37° C. and 5% $CO_2$/95% air.

3. Cell Proliferation and Viability Assay

3.1 MTS Assay

Cell proliferation was determined by MTS (tetrazolium compound, 3-(4,5-dimethylthiazol-2-yl)-5-(3-carboxymethoxyphenyl)-2-(4-sulfophenyl)-2H-tetrazolium) assay (Promega). MTS assay is a colorimetric assay for determining cell viability (Mosmann, T. (1983). Rapid colorimetric assay for cellular growth and survival: application to proliferation and cytotoxicity assays. *J Immunol Methods* 65, 55-63). The MTS tetrazolium compound is bio-reduced by NADPH or NADH produced by dehydrogenase in live cells into a colored formazan product. $1 \times 10^3$ Cells were seeded in each well of 96-well plates for MTS assay and cells were incubated for 24 hr. Culture media containing sequential concentrations of MJ-66, MJ-68 and MJ-78 (1, 0.1, 0.05, 0.025, 0.0125 and 0.00625 µM) or DMSO (0.1%) were added to each well, and cells were incubated at 37° C. At the indicated time points (0, 24, 48 and 72 hr), media were removed, and then fresh culture media (100 µl/well) with MTS solution (20 µl/well) were added, and cells were incubated at 37° C. for 1-4 hr. The absorbance of soluble formazan was measured at 490 nm with microplate reader (Molecular device). The cell viability was determined by the percentage of the absorption relative to untreated control. All results were performed from three independent experiments.

3.2 MTT Assay

Cells ($1 \times 10^4$ cells/well) in 96-well plates were exposed to test MJ-66, and 0.1% DMSO in media served as a vehicle control. After 24 and 48 hr-incubations, 100 ml MTT (0.5 mg/mL) solution was added to each well, the plate was incubated at 37° C. for 4 hours. Then, 100 ml 0.04 N HCl in isopropanol was added and the absorbance at 570 nm was measured for each well. The cell survival rate was expressed as % of control. All results were performed from three independent experiments.

3.3 Trypan-Blue Exclusion Assay

Cell viability was also determined by trypan-blue exclusion assay. Cells were seeded in 6-well plates ($2 \times 10^4$/well) for trypan blue exclusion assay, and incubated for 24 hours at 37° C. Culture medium containing test compound or DMSO (0.006%) was added to each well, and cells were incubated at 37° C. At indicated time points (0, 24, 48, 72 and 96 hr), cells were suspended with 0.05% trypsin-EDTA, and stained with trypan-blue dye (0.4%) (Sigma). The cell viability was evaluated by the percentage of death relative to the total cell, and cell growth curve was determined by number of live cells relative to the total number of cells.

4. Cell Cycle Assay

To analyze cellular DNA content by flow cytometry, $3 \times 10^5$ cells were seeded in 10 cm dish and incubated for 24 hours at 37° C. Culture medium containing MJ-66 ($IC_{50}$) or DMSO (0.006%) was added, and cells were incubated for 24 hours at 37° C. At indicated time points (0, 6, 12, 24 and 48 hr), over $10^6$ cells were suspended with 0.05% trypsin-EDTA, and fixed in 70% ethanol over 1 hour at −20° C. After washed by phosphate-buffered saline (PBS) twice, cells were then suspended with 1 ml propidium iodide/Triton-X 100 staining solution (20 µg/ml PI, 0.1% Triton-X 100 and 0.2 mg/ml ribonuclease A (RNase A, Sigma) in PBS) and incubated for 30 minutes at room temperature in the dark. After filtered by 35 µm nylon mesh (Falcon, 352235), the DNA content was then analyzed by flow cytometry (FACS can, BD Bioscience). The cell-cycle distribution (subG1, G1, S, G2/M, and >4N DNA content) of ten thousand cells was analyzed by WinMDI software.

5. G1 Synchronized by Ara-C

To analyze the effect of cytosine arabinoside (Ara-C, a DNA synthesis inhibitor) on the MJ-66-treated glioma cells by flow cytometry, after seeding $3 \times 10^5$ cells in 10 cm-plate for at least 24 hours at 37° C., glioma cells were then treated with Ara-C (4.17 mM/ml) for 12 hours, and then MJ-66 ($IC_{50}$) or DMSO (0.006%) was added. At indicated time points (0, 6, 12 and 24 hr), $>10^6$ cells were collected and fixed in 70% ethanol over 1 hour at −20° C. After staining with PI as described, DNA content of ten thousand cells was analyzed by flow cytometry.

6. Immunofluorescent Staining $2 \times 10^4$ cells were seeded on the PDL-coating 12 mm-glass coverslips in 24-well plate and allowed to attach for 24 hours at 37° C. Culture medium containing MJ-66 ($IC_{50}$) or DMSO (0.006%) was added, and cells were incubated at 37° C. At indicated time points (0, 12 and 24 hr), cells were fixed in 4% paraformaldehyde (PFA) in PBS for 30 minutes. After permeabilized by 0.2% Triton X-100 in 0.1 M PBS for 10 minutes and 10% methanol containing 0.2% Triton X-100 in 0.1 M PBS for 5 minutes, cells were blocked in 3% bovine serum albumin (BSA, Sigma) for 1 hour. The cells were immunostained for mitotic spindle with mouse monoclonal alpha-tubulin (Sigma-Aldrich), and mitotic center with rabbit polyclonal gamma-tubulin (Genetex), and then stained with appropriated secondary antibodies conjugated with Texas Red or FITC for 1 hr. Nuclei were stained with Hoechst 33342 for 10 minutes (0.5 µg/ml, Sigma-Aldrich, B2261). Fluorescence images were detected by confocal laser scanning microscope (FV1000, Olympus).

7. In Vivo Xenograft Animal Model

For tumorigenesis, U87 glioma cells ($1\times10^6$ cells per 100 µl PBS) were inoculated subcutaneously into the right flank of 8-to-10-week-old male nude mice (BALB/cAnN-Foxnlnu/CrlNarl mice, National Laboratory Animal Center, Taiwan). Tumor growth was measured every three days. Tumor volume was calculated by volume $(mm^3)=(length\times width^2)/2$ (Zhou, Y. H., Wu, X., Tan, F., Shi, Y. X., Glass, T., Liu, T. J., Wathen, K., Hess, K. R., Gumin, J., Lang, F., et al. (2005). PAX6 suppresses growth of human glioblastoma cells. *J Neurooncol* 71, 223-229.). When the tumors reached a mean volume of 50 to 70 $mm^3$, MJ-66 (1.36 microgram/kg in saline) or vehicle (DMSO or saline) was injected intratumor once per two days during 20 days.

8. Statistical Analysis

Experiments were performed at least in triplicate. All results were expressed as the mean±standard error of the mean. Independent experiments were analyzed by unpaired t test. Levels of $P<0.05$ were considered to be of statistical significance.

Preparation Example 1

General Procedure for Synthesis of Starting 5-substituted-2-aminobenzamides (9-13) by Schemes 1 and 2

Starting 2-nitrobenzamide for synthesis of 2-aryl-4-quinazolinone of formula I in accordance with the present invention was prepared as follows.

5-Substituted-2-nitrobenzamide (2, 5-8) was prepared using standard methodology from 5-substituted-2-nitrobenzoic acid (1, 3) by reaction with reagents, such as $SOCl_2$, $NH_3$, and dimethylamine (or pyrrolidine, piperidine, morpholine), under a condition as shown in the general reaction sequence in Schemes 1 and 2. Compounds 2 and 5-8 were treated with $H_2$/Pd—C in methanol to afford 5-substituted-2-aminobenzamide (9-13).

Scheme 1

Reagents and conditions:
a. (i) $SOCl_2$, reflux (ii) $NH_3$ (g), dichloroethane, RT
b. dimethylamine (or pyrrolidine, piperidine, morpholine), DMF, 110° C.

The procedure for synthesis of 5-substituted-2-aminobenzamides was performed as follows:

(a) (i) Thionyl chloride (1.5 g, 12.6 mmol) was added dropwise to a suspension of a 5-substituted-2-nitrobenzoic acid (1: 1.2 g, 6.3 mmol; 3: 1.3 g, 6.3 mmol) in dichloroethane (30 mL) under reflux. The resulting mixture was stirred under reflux for 4 hours and dried under vacuum. (ii) The residue was dissolved in 200 mL of dichloroethane and treated with anhydrous ammonia gas at room temperature. After removing solvent, the intermediate 5-methoxy-2-nitrobenzamide (2: 1.1 g, 92%) or 5-chloro-2-nitrobenzamide (4: 1.2 g, 92%) was obtained.

(b) The intermediate 4 was dissolved in DMF and reacted with N,N-dimethylamine (or pyrrolidine or piperidine or morpholine) at 110° C. to afford 5-substituted-2-nitrobenzamides (5: 1.1 g, 88%; 6: 1.2 g, 86%; 7: 1.2 g, 80%; 8: 1.2 g, 81%). (c) The 5-substituted-2-nitrobenzamides (2, 5-8) was dissolved in MeOH and hydrogenated over 10% Pd/C for 1 to 2 hours. The catalyst was removed by filtration, and the solution was dried under vacuum to afford the 5-substituted-2-aminobenzamides 9-13 (9: 0.8 g, 86%; 10: 0.9 g, 85%; 11: 0.9 g, 85%; 12: 0.9 g, 82%; 13: 0.9 g, 82%) as brown powders.

Preparation Example 2

General Procedure for Synthesis of 6-substituted-2-aryl-4-quinazolinones 6-substituted-2-aryl-4-quinazolinones were derived from Compounds 9-13 obtained in Preparation example 1 in this example. First, compounds 9-13 then were respectively reacted with substituted benzaldehydes in N,N-dimethylacetamide (DMAC) in the presence of $NaHSO_3$ at 150° C. Then, Thermal cyclodehydration/dehydrogenation gave the 2,6-disubstituted-4-quinazolinones (17-31) as shown in scheme 3.

-continued

R6-C6H3(NH2)(CONH2) + H-C(=O)-R2 →[b, 14-16] R6-quinazolin-4(3H)-one-2-R2

9-13 → 17-31

Reagents and conditions:
a. H₂, Pd/C, methanol
b. NaHSO₃, DMAC, 150° C.

2, 9, 17-19  R₆ = OCH₃

5, 10, 20-22  R₆ = N(CH₃)₂

6, 11, 23-25  R₆ = pyrrolidinyl 7, 12, 26-28  R₆ = piperidinyl 8, 13, 29-31  R₆ = morpholinyl 14, 17, 20, 23, 26, 29  R₂ = naphthalen-1-yl 15, 18, 21, 24, 27, 30  R₂ = 1H-indol-3-yl 16, 19, 22, 25, 28, 31  R₂ = benzo[b]thiophen-3-yl The procedure for synthesis of 6-substituted-2-aryl-4-quinazolinones was performed as follows:

Sodium hydrogen sulfite (0.8 g, 7.5 mmol) was added to a solution of 5-methoxy-2-aminobenzamide (9) (1.2 g, 7.3 mmol) and 1-naphthaldehyde (14) (1.1 g, 7.3 mmol) in N,N-dimethylacetamide (DMAC) (20 mL). The mixture was heated with stirring at 150° C. for 3 h and poured into ice water (200 mL). The precipitate was collected, washed with water, and dried in vacuo. After purification by column chromatography (silica gel; chloroform) and then recrystallization from EtOH, 6-methoxy-2-(naphthalen-1-yl)-4-quinazolinone (17) was obtained (1.5 g, 70%) as pale yellow needles. The method used to prepare 17 was used with the indicated substituted benzaldehyde and benzamide to afford 18-31. Compounds 17-31 were further analyzed by the method as described in "General materials and method". The properties of Compounds 17-31 were respectively described as below.

Example 1

6-Methoxy-2-(naphthalen-1-yl) quinazolin-4-one (17)

Compound 17 was synthesized from 5-methoxy-2-aminobenzamide (9) (1.2 g, 7.3 mmol) and 1-naphthaldehyde (14) (1.1 g, 7.3 mmol): yield 1.5 g (70%); pale yellow needles; mp 174 to 175° C.; $^1$H NMR (DMSO-$d_6$) δ 3.87 (3H, s, OCH₃), 7.22-7.34 (2H, m, 2×ArH), 7.53-7.72 (5H, m, 5×ArH), 7.95-8.22 (3H, m, 3×ArH), 12.62 (1H, br s, NH) ppm; MS (ESI) m/z 302; Anal. ($C_{19}H_{14}N_2O_2$): C, H, N.

Example 2

6-Methoxy-2-(1H-indol-3-yl)quinazolin-4-one (18)

Compound 18 was synthesized from 5-methoxy-2-aminobenzamide (9) (1.2 g, 7.3 mmol) and indo-3-carboxaldehyde (15) (1.1 g, 7.3 mmol): yield 1.4 g (68%); brown crystals; mp 311 to 312° C.; $^1$H NMR (DMSO-$d_6$) δ 3.84 (3H, s, OCH₃), 7.15-7.19 (2H, m, 2×ArH), 7.35-7.49 (3H, m, 3×ArH), 7.63-7.68 (1H, m, 1×ArH), 8.45 (1H, s, 1×ArH), 8.46-8.63 (1H, m, 1×ArH), 11.76 (1H, s, NH), 12.11 (1H, br s, NH) ppm; MS (ESI) m/z 291; Anal. ($C_{17}H_{13}N_3O_2$); C, H, N.

Example 3

6-Methoxy-2-(benzo[b]thiophen-3-yl)quinazolin-4-one (19)

Compound 19 was synthesized from 5-methoxy-2-aminobenzamide (9) (1.2 g, 7.3 mmol) and thianaphthene-3-carboxaldehyde (16) (1.2 g, 7.3 mmol): yield 1.3 g (60%); brown crystals; mp 289 to 290° C.; $^1$H NMR (DMSO-$d_6$) δ 3.89 (3H, s, OCH₃), 7.43-7.57 (4H, m, 4×ArH), 7.76-7.80 (1H, m, 1×ArH), 8.07-8.11 (1H, m, 1×ArH), 8.73 (1H, s, 1×ArH), 8.98-9.01 (1H, m, 1×ArH), 12.49 (1H, br s, NH) ppm; MS (ESI) m/z 308; Anal. ($C_{17}H_{12}N_2O_2S$): C, H, N.

Example 4

6-(N,N-Dimethylamino)-2-(naphthalen-1-yl)quinazolin-4-one (20)

Compound 20 was synthesized from 5-N,N-dimethyl-2-aminobenzamide (10) (1.3 g, 7.3 mmol) and 1-naphthaldehyde (14) (1.1 g, 7.3 mmol): yield 1.5 g (65%); yellow crystals; mp 254 to 255° C.; $^1$H NMR (DMSO-$d_6$) δ 2.99 (6H, s, N(CH₃)₂), 7.22-7.34 (2H, m, 2×ArH), 7.51-7.72 (5H, m, 5×ArH), 7.96-8.23 (3H, m, 3×ArH), 12.39 (1H, br s, NH) ppm; MS (ESI) m/z 315; Anal. ($C_{20}H_{17}N_3O$): C, H, N.

Example 5

6-(N,N-Dimethylamino)-2-(1H-indol-3-yl)quinazolin-4-one (21)

Compound 21 was synthesized from 5-N,N-dimethyl-2-aminobenzamide (10) (1.3 g, 7.3 mmol) and indo-3-carboxaldehyde (15) (1.1 g, 7.3 mmol): yield 1.3 g (60%); yellow crystals; mp>300° C.; $^1$H NMR (DMSO-$d_6$) δ 2.99 (6H, s, N(CH₃)₂), 7.17-7.34 (4H, m, 4×ArH), 7.43-7.47 (1H, m, 1×ArH), 7.58-7.63 (1H, m, 1×ArH), 8.44 (1H, s, 1×ArH), 8.65-8.69 (1H, m, 1×ArH), 11.71 (1H, s, NH), 11.92 (1H, br s, NH) ppm; MS (ESI) m/z 304; Anal. ($C_{18}H_{16}N_4O$): C, H, N.

Example 6

6-(N,N-Dimethylamino)-2-(benzo[b]thiophen-3-yl)quinazolin-4-one (22)

Compound 22 was synthesized from 5-N,N-dimethyl-2-aminobenzamide (10) (1.3 g, 7.3 mmol) and thianaphthene-3-carboxaldehyde (16) (1.2 g, 7.3 mmol): yield 1.5 g (62%); pale yellow needles; mp>300° C.; $^1$H NMR (DMSO-$d_6$) δ 2.99 (6H, s, N(CH$_3$)$_2$), 7.20-7.67 (5H, m, 5×ArH), 8.02-8.05 (1H, m, 1×ArH), 8.63 (1H, s, 1×ArH), 8.97-9.01 (1H, m, 1×ArH), 12.21 (1H, br s, NH) ppm; MS (ESI) m/z 321; Anal. ($C_{18}H_{15}N_3OS$): C, H, N.

Example 7

6-(Pyrrolidin-1-yl)-2-(naphthalen-1-yl)quinazolin-4-one (23) (MJ-66)

Compound 23 was synthesized from 5-pyrrolidinyl-2-aminobenzamide (11) (1.5 g, 7.3 mmol) and 1-naphthaldehyde (14) (1.1 g, 7.3 mmol): yield 1.6 g (65%); pale yellow needles; mp 276 to 277° C.; $^1$H NMR (DMSO-$d_6$) δ 1.99 (4H, m, C$\underline{H}_2$CH$_2$NCH$_2$C$\underline{H}_2$), 3.27 (4H, m, CH$_2$NCH$_2$), 7.10-7.21 (2H, m, 2×ArH), 7.56-7.76 (5H, m, 5×ArH), 8.01-8.21 (3H, m, 3×ArH), 12.34 (1H, br s, NH) ppm; MS (ESI) m/z 341; Anal. ($C_{22}H_{19}N_3O$): C, H, N.

Example 8

6-(Pyrrolidin-1-yl)-2-(1H-indol-3-yl)quinazolin-4-one (24)

Compound 24 was synthesized from 5-pyrrolidinyl-2-aminobenzamide (11) (1.5 g, 7.3 mmol) and indo-3-carboxaldehyde (15) (1.1 g, 7.3 mmol): yield 1.5 g (61%); brown powders; mp 298° C.; $^1$H NMR (DMSO-$d_6$) δ 1.94 (4H, m, C$\underline{H}_2$CH$_2$NCH$_2$C$\underline{H}_2$), 3.28 (4H, m, CH$_2$NCH$_2$), 6.97-7.20 (4H, m, 4×ArH), 7.39-7.43 (1H, m, 1×ArH), 7.53-7.58 (1H, m, 1×ArH), 8.38 (1H, s, 1×ArH), 8.61-8.65 (1H, m, 1×ArH), 11.68 (1H, s, NH), 11.88 (1H, br s, NH) ppm; MS (ESI) m/z 330; Anal. ($C_{20}H_{18}N_4O$): C, H, N.

Example 9

6-(Pyrrolidin-1-yl)-2-(benzo[b]thiophen-3-yl)quinazolin-4-one (25) (MJ-78)

Compound 25 was synthesized from 5-pyrrolidinyl-2-aminobenzamide (11) (1.5 g, 7.3 mmol) and thianaphthene-3-carboxaldehyde (16) (1.2 g, 7.3 mmol): yield 1.5 g (60%); brown powders; mp>300° C.; $^1$H NMR (DMSO-$d_6$) δ 1.97 (4H, m, C$\underline{H}_2$CH$_2$NCH$_2$C$\underline{H}_2$), 3.47 (4H, m, CH$_2$NCH$_2$), 7.43-7.57 (4H, m, 4×ArH), 7.76-7.80 (1H, m, 1×ArH), 8.07-8.11 (1H, m, 1×ArH), 8.73 (1H, s, 1×ArH), 8.98-9.02 (1H, m, 1×ArH), 12.51 (1H, br s, NH) ppm; MS (ESI) m/z 347; Anal. ($C_{20}H_{17}N_3OS$): C, H, N.

Example 10

6-(Piperidin-1-yl)-2-(naphthalen-1-yl)quinazolin-4-one (26) (MJ-68)

Compound 26 was synthesized from 5-piperidinyl-2-aminobenzamide (12) (1.6 g, 7.3 mmol) and 1-naphthaldehyde (14) (1.1 g, 7.3 mmol): yield 1.6 g (65%); brown needles; mp 233 to 235° C.; $^1$H NMR (DMSO-$d_6$) δ 1.57-1.62 (6H, m, (C$\underline{H}_2$)$_2$CH$_2$NCH$_2$C$\underline{H}_2$), 3.26-3.31 (4H, m, CH$_2$NCH$_2$), 7.48-7.65 (6H, m, 6×ArH), 7.72-7.76 (1H, m, 1×ArH), 8.00-8.13 (3H, m, 3×ArH), 12.43 (1H, br s, NH) ppm; MS (ESI) m/z 355; Anal. ($C_{23}H_{21}N_3O$): C, H, N.

Example 11

6-(Piperidin-1-yl)-2-(1H-indol-3-yl)quinazolin-4-one (27)

Compound 27 was synthesized from 5-piperidinyl-2-aminobenzamide (12) (1.6 g, 7.3 mmol) and indo-3-carboxaldehyde (15) (1.1 g, 7.3 mmol): yield 1.6 g (64%); brown crystals; mp>300° C.; $^1$H NMR (DMSO-$d_6$) δ 1.59-1.62 (6H, m, (C$\underline{H}_2$)$_2$CH$_2$NCH$_2$C$\underline{H}_2$), 3.20-3.24 (4H, m, CH$_2$NCH$_2$), 7.18-7.21 (2H, m, 2×ArH), 7.41-7.48 (3H, m, 3×ArH), 7.50-7.62 (1H, m, 1×ArH), 8.46 (1H, s, 1×ArH), 8.65-8.69 (1H, m, 1×ArH), 11.73 (1H, s, NH), 11.96 (1H, br s, NH) ppm; MS (ESI) m/z 344; Anal. ($C_{21}H_{20}N_4O$): C, H, N.

Example 12

6-(Piperidin-1-yl)-2-(benzo[b]thiophen-3-yl)quinazolin-4-one (28)

Compound 28 was synthesized from 5-piperidinyl-2-aminobenzamide (12) (1.6 g, 7.3 mmol) and thianaphthene-3-carboxaldehyde (16) (1.2 g, 7.3 mmol): yield 1.6 g (60%); pale yellow crystals; mp>300° C.; $^1$H NMR (DMSO-$d_6$) δ 1.57-1.59 (6H, m, (C$\underline{H}_2$)$_2$CH$_2$NCH$_2$C$\underline{H}_2$), 3.22-3.25 (4H, m, CH$_2$NCH$_2$), 7.42-7.54 (4H, m, 4×ArH), 7.63-7.67 (1H, m, 1×ArH), 8.03-8.07 (1H, m, 1×ArH), 8.66 (1H, s, 1×ArH), 8.97-9.00 (1H, m, 1×ArH), 12.30 (1H, br s, NH) ppm; MS (ESI) m/z 361; Anal. ($C_{21}H_{19}N_3OS$): C, H, N.

Example 13

6-(Morpholino)-2-(naphthalen-1-yl)quinazolin-4-one (29)

Compound 29 was synthesized from 5-morpholinyl-2-aminobenzamide (13) (1.6 g, 7.3 mmol) and 1-naphthaldehyde (14) (1.1 g, 7.3 mmol): yield 1.7 g (64%); yellow crystals; mp 291 to 293° C.; $^1$H NMR (DMSO-$d_6$) δ 3.22 (4H, t, J=4.7 Hz, CH$_2$NCH$_2$), 3.77 (4H, t, J=4.7 Hz, CH$_2$OCH$_2$), 7.51-7.66 (6H, m, 6×ArH), 7.73-7.76 (1H, m, 1×ArH), 8.00-8.11 (3H, m, 3×ArH), 12.48 (1H, br s, NH) ppm; MS (ESI) m/z 357; Anal. ($C_{22}H_{19}N_3O_2$): C, H, N.

Example 14

6-(Morpholino)-2-(1H-indol-3-yl)quinazolin-4-one (30)

Compound 30 was synthesized from 5-morpholinyl-2-aminobenzamide (13) (1.6 g, 7.3 mmol) and indo-3-carboxaldehyde (15) (1.1 g, 7.3 mmol): yield 1.6 g (65%); brown crystals; mp>300° C.; $^1$H NMR (DMSO-$d_6$) δ 2.97 (4H, t, J=4.7 Hz, CH$_2$NCH$_2$), 3.74 (4H, t, J=4.7 Hz, CH$_2$OCH$_2$), 7.12-7.22 (2H, m, 2×ArH), 7.41-7.63 (4H, m, 4×ArH), 8.43 (1H, s, 1×ArH), 8.60-8.64 (1H, m, 1×ArH), 11.76 (1H, s, NH), 12.01 (1H, br s, NH) ppm; MS (ESI) m/z 346; Anal. ($C_{20}H_{18}N_4O_2$): C, H, N.

Example 15

6-(Morpholino)-2-(benzo[b]thiophen-3-yl)quinazolin-4-one (31)

Compound 31 was synthesized from 5-morpholinyl-2-aminobenzamide (13) (1.6 g, 7.3 mmol) and thianaphthene-3-carboxaldehyde (16) (1.2 g, 7.3 mmol): yield 1.6 g (60%); brown crystals; mp>300° C.; $^1$H NMR (DMSO-d$_6$) δ 2.47 (4H, t, J=4.7 Hz, CH$_2$NCH$_2$), 3.75 (4H, t, J=4.7 Hz, CH$_2$OCH$_2$), 7.44-7.59 (4H, m, 4×ArH), 7.67-7.72 (1H, m, 1×ArH), 8.03-8.07 (1H, m, 1×ArH), 8.67 (1H, s, 1×ArH), 8.96-9.00 (1H, m, 1×ArH), 12.31 (1H, br s, NH) ppm; MS (ESI) m/z 363; Anal. (C$_{20}$H$_{17}$N$_3$O$_2$S): C, H, N.

Example 16

In vitro cytotoxicity of 2-Aryl-4-quinazolinones

2-Aryl-4-quinazolinones prepared in Examples 1 to 15, Compounds 17-31, were listed in the following Table 1, denoted as MJ-66 to −80 and identified by their molecular weight.

TABLE 1

| Item (Compound) | Structure | Formula | Molecular weight |
|---|---|---|---|
| MJ-65 (24) | | C$_{20}$H$_{18}$N$_4$O | 330 |
| MJ-66 (23) | | C$_{22}$H$_{19}$N$_3$O | 341 |
| MJ-67 (29) | | C$_{22}$H$_{19}$N$_3$O$_2$ | 357 |
| MJ-68 (26) | | C$_{23}$H$_{21}$N$_3$O | 355 |
| MJ-69 (20) | | C$_{20}$H$_{17}$N$_3$O | 315 |

TABLE 1-continued

| Item (Compound) | Structure | Formula | Molecular weight |
|---|---|---|---|
| MJ-70 (17) | | $C_{19}H_{14}N_2O_2$ | 302 |
| MJ-72 (27) | | $C_{21}H_{20}N_4O$ | 344 |
| MJ-73 (28) | | $C_{21}H_{19}N_3OS$ | 361 |
| MJ-74 (18) | | $C_{17}H_{13}N_3O_2$ | 291 |
| MJ-75 (21) | | $C_{18}H_{16}N_4O$ | 304 |
| MJ-76 (30) | | $C_{20}H_{18}N_4O_2$ | 346 |

TABLE 1-continued

| Item (Compound) | Structure | Formula | Molecular weight |
|---|---|---|---|
| MJ-77 (31) | [structure: morpholino-substituted 2-(benzothiophen-3-yl)quinazolin-4(3H)-one] | $C_{20}H_{17}N_3O_2S$ | 363 |
| MJ-78 (25) | [structure: pyrrolidino-substituted 2-(benzothiophen-3-yl)quinazolin-4(3H)-one] | $C_{20}H_{17}N_3OS$ | 347 |
| MJ-79 (19) | [structure: 6-methoxy-2-(benzothiophen-3-yl)quinazolin-4(3H)-one] | $C_{17}H_{12}N_2O_2S$ | 308 |
| MJ-80 (22) | [structure: 6-dimethylamino-2-(benzothiophen-3-yl)quinazolin-4(3H)-one] | $C_{18}H_{15}N_3OS$ | 321 |

The anti-proliferation effects of Compounds 17-31 on M21, CH27, H460, Hep3B and HSC-3 cells were evaluated by the trypan blue exclusion assay. The results, $IC_{50}$ values of Compounds 17-31 on cancer cell lines, are presented in Table 2. The results demonstrated that the Compounds 17, 20, 23, 24, 26, 27 and 29 exhibited cytotoxic effects toward these cancer cells, but compound 17 was inactive on HSC-3 cells. Among them, Compound 23, that is, MJ-66, was the most potent compound against these human cancer cells in vitro.

TABLE 2

In vitro cytotoxicity of 2-Aryl-4-quinazolinones

| Compound | $IC_{50}$ (μM)* | | | | |
|---|---|---|---|---|---|
| | M21 | CH27 | H460 | Hep3B | HSC-3 |
| 17 | 6.093 | 0.089 | 0.079 | 1.870 | >10 |
| 18 | >10 | >10 | >10 | >10 | >10 |
| 19 | >10 | >10 | >10 | >10 | >10 |
| 20 | 3.775 | 0.447 | 0.506 | 8.626 | 0.202 |
| 21 | >10 | >10 | >10 | >10 | >10 |
| 22 | >10 | >10 | >10 | >10 | >10 |
| 23 | 0.033 | 0.053 | 0.075 | 1.350 | 0.041 |
| 24 | 7.629 | 8.700 | 8.810 | 7.390 | 1.890 |
| 25 | >10 | >10 | >10 | >10 | >10 |
| 26 | 1.587 | 0.362 | 0.376 | 7.235 | 1.730 |
| 27 | 8.989 | >10 | 6.862 | 5.653 | >10 |
| 28 | >10 | >10 | >10 | >10 | >10 |
| 29 | 2.333 | 0.597 | 0.432 | 1.056 | 0.614 |
| 30 | >10 | >10 | >10 | >10 | >10 |
| 31 | >10 | >10 | >10 | >10 | >10 |

*$IC_{50}$: half maximal inhibitory concentration; M21: skin cancer, CH27: human lung squamous carcinoma, H460: human non-small cell lung cancer, Hep3B: human hepatoma, HSC-3: human squamous carcinoma; Cell viability was determined by trypan blue exclusion assay.

Example 17

Figure 1:
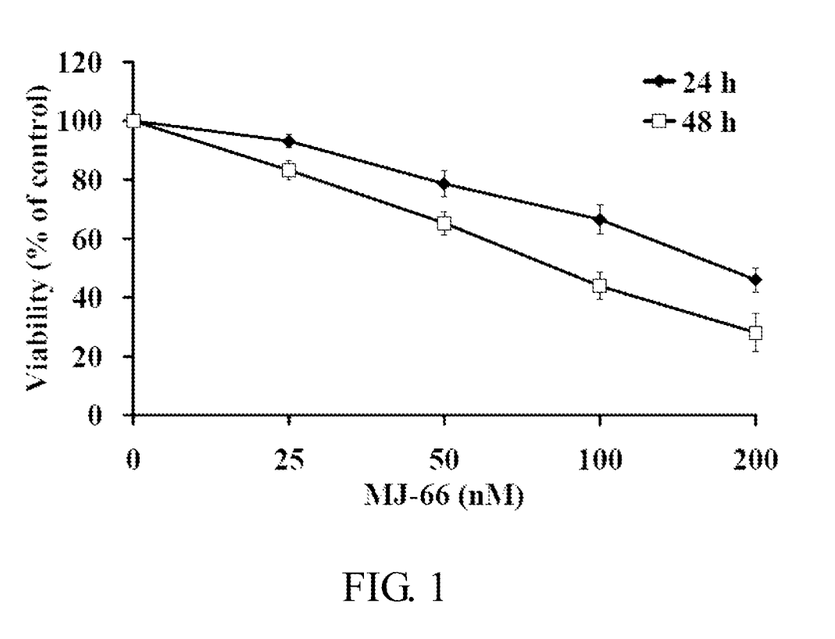
FIG. 1 illustrates the effect of MJ-66 on cell viability in HT29-5FUR cells.

2-Aryl-4-quinazolinone (MJ-66) inhibited HT29-5FUR cells (human colon adenocarcinoma) proliferation The growth inhibition effects of MJ-66 on HT29-5FUR cells were investigated. For cell viability assay, HT29-5FUR cells were cultured and treated with 0, 25, 50, 100 and 200 nM MJ-66 and the percentages of viable cells were detected by MTT assay described in "General materials and methods".

As shown in FIG. 1, exposure to various concentrations of MJ-66 (25, 50, 100 and 200 nM) for 24 and 48 hours (denoted as 24 h and 48 h) resulted in dose-dependent decreases on cell number of HT29-5FUR relative to control cultures.

Example 18

2-Aryl-4-quinazolinones inhibited glioma cells proliferation

Figure 2:
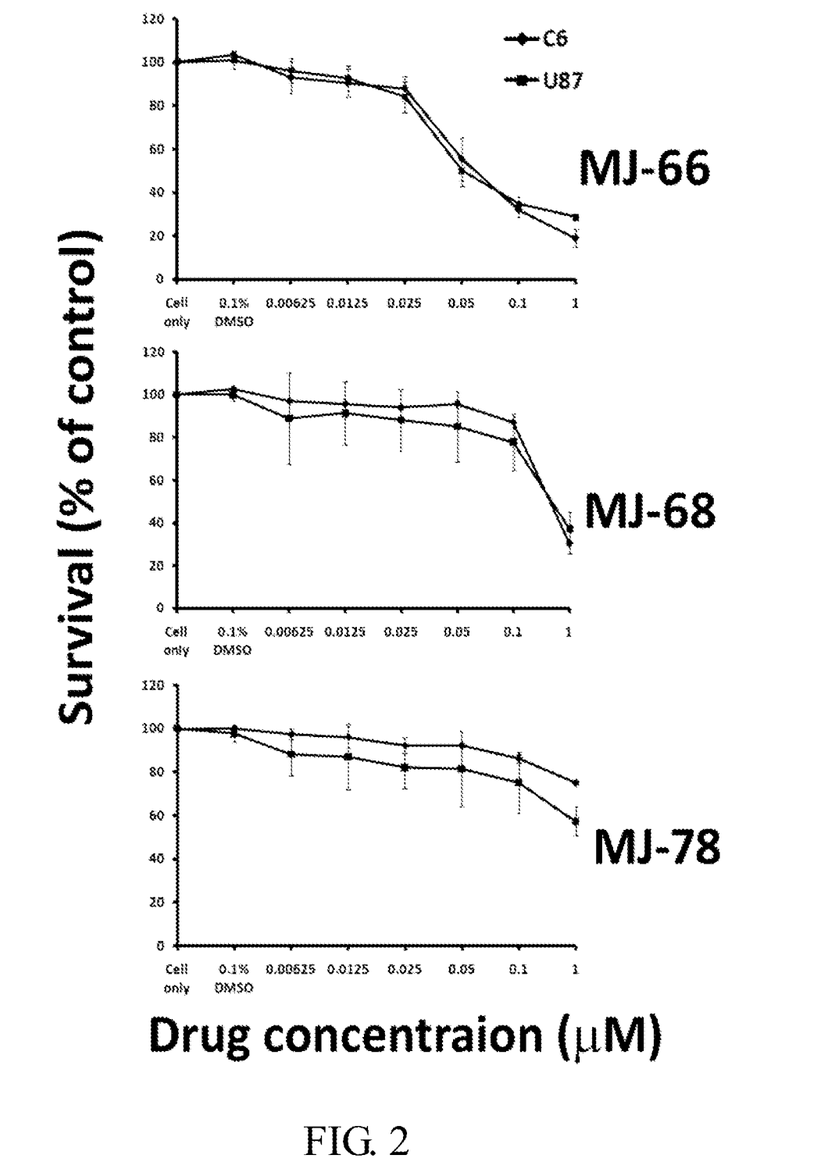
FIG. 2 illustrates concentration-dependent effects of MJ-66, MJ-68 and MJ-78 on glioma cell lines including C6 and U87 for 48 hr (mean±SEM, n=3), wherein C6 represents rat glioma cells and U87 represents human glioma cells.

To investigate the effect of 2-aryl-4-quinazolinone in accordance with the present invention on cell proliferation, glioma cell lines were treated with MJ-66, MJ-68, or MJ-78. Structures of MJ-66, MJ-68 and MJ-78 were shown in Table 1. To determine the effects among MJ-66, MJ-68, and MJ-78 on C6 rat glioma (denoted as C6) and U87 human glioma cell lines (denoted as U87), cells were treated with different concentrations of the 2-aryl-4-quinazolinone (0.00625, 0.0125, 0.025, 0.05, 0.1 and 1 µM) for 48 hours. The cell viability of each group was analyzed by MTS assay (mean±SEM, n=3). As shown in FIG. 2B, survival rates of glioma cells were effectively inhibited by MJ-66 at the 48th hr. ($IC_{50}$ values MJ-66, C6=0.056±0.009 µM, U87=0.054±0.01 µM).

Even though numerous characteristics and advantages of the present invention have been set forth in the foregoing description, together with details of the features of the invention, the disclosure is illustrative only. Changes may be made in the details within the principles of the invention to the full extent indicated by the broad general meaning of the terms in which the appended claims are expressed.

What is claimed is:

1. A compound of the formula I or a pharmaceutically acceptable salt, solvate, or stereoisomer thereof:

formula I wherein $R_5$, $R_7$ and $R_8$ independently represent H, OH, F, Cl, Br methoxyl group, $NH_2$ group or $NMe_2$ group;
Ar represents $R_2'$, $R_3'$, $R_4'$, $R_5'$, $R_6'$, $R_7'$, $R_8'$ independently represent H, OH, F, Cl, Br, methoxyl group, $NH_2$ group or $NMe_2$ group;
wherein $R_6$ is selected from the group consisting of: piperidinyl group, pyrrolidinyl group, morpholino group, methoxyl group, and N,N-dimethylamino group.

2. The compound as claimed in claim 1 or a pharmaceutically acceptable salt, solvate or stereoisomer thereof, which is:

,

,

, or

.

3. A composition, which comprises a compound as claimed in claim 1 or a pharmaceutically acceptable salt, solvate or stereoisomer thereof; and a carrier.

4. The composition of claim 3, wherein the compound is,

,

5. A method for treating cancer in a subject comprising: administering to said subject a pharmaceutical composition comprising a compound selected from the group consisting of:

or a pharmaceutically acceptable salt, solvate or stereoisomer thereof.

6. The method as claimed in claim 5, wherein the cancer is selected from the group consisting of: skin, lung, lymph node, breast, cervix, uterus, gastrointestinal tract, ovary, prostate, colorectal, mouth, brain, head and neck, throat, testes, kidney, pancreas, bone, spleen, liver, bladder, larynx and nasal passage cancers and tumors.

7. The method as claimed in claim 5, wherein the cancer is malignant glioma, sarcoma, carcinoma or adenoma.

* * * * *